United States Patent

Effenhauser

[11] Patent Number: 6,032,073
[45] Date of Patent: Feb. 29, 2000

[54] IONTOPHORETIC TRANSDERMAL SYSTEM FOR THE ADMINISTRATION OF AT LEAST TWO SUBSTANCES

[75] Inventor: Carlo Stefan Effenhauser, Freiburg, Germany

[73] Assignee: Novartis AG, Basel, Switzerland

[21] Appl. No.: 08/930,720

[22] PCT Filed: Mar. 26, 1996

[86] PCT No.: PCT/EP96/01327

§ 371 Date: Dec. 15, 1997

§ 102(e) Date: Dec. 15, 1997

[87] PCT Pub. No.: WO96/31251

PCT Pub. Date: Oct. 10, 1996

[30] Foreign Application Priority Data

Apr. 7, 1995 [EP] European Pat. Off. .............. 95810232

[51] Int. Cl.⁷ .................................................. A61N 1/30
[52] U.S. Cl. .......................................................... 604/20
[58] Field of Search .............................. 604/20, 19, 289, 604/890.1; 607/115, 120, 152, 153

[56] References Cited

U.S. PATENT DOCUMENTS

| | | | |
|---|---|---|---|
| 4,734,090 | 3/1988 | Sibalis | 604/20 |
| 5,053,001 | 10/1991 | Reller et al. | 604/20 |
| 5,207,752 | 5/1993 | Sorenson et al. | 604/20 |
| 5,310,404 | 5/1994 | Gyory et al. | 604/20 |
| 5,427,585 | 6/1995 | Bettinger | 604/20 |
| 5,464,387 | 11/1995 | Haak et al. | 604/20 |
| 5,668,170 | 9/1997 | Gyory | 604/20 |
| 5,695,459 | 12/1997 | Meguro | 604/20 |
| 5,795,321 | 8/1998 | McArthur et al. | 604/20 |

FOREIGN PATENT DOCUMENTS

| | | |
|---|---|---|
| 0252732 | 1/1988 | European Pat. Off. . |
| 9115261 | 10/1991 | WIPO . |
| 9210234 | 6/1992 | WIPO . |

*Primary Examiner*—Wynn Wood Coggins
*Assistant Examiner*—Sharon Finkel
*Attorney, Agent, or Firm*—Gabriel Lopez; William K. Wissing

[57] ABSTRACT

A transdermal system (1) for the administration of at least two substances through the skin with the aid of an electric current has a reservoir, which comprises a storage layer (2) for the substances, and a transfer means, which may be arranged in the form of a separating layer (3), that is connected to both the reservoir and the patient's skin (5) during administration. The transdermal system also has electrodes (4) which generate a current that transports the substances from the reservoir into the skin (5). In the transdermal system (1) means for the physical separation of the substances are provided that render possible a sequential administration of the substances.

18 Claims, 2 Drawing Sheets

6,032,073

IONTOPHORETIC TRANSDERMAL SYSTEM FOR THE ADMINISTRATION OF AT LEAST TWO SUBSTANCES

This is a 371 of International Application PCT/EP 96/01327, filed Mar. 26, 1996.

BACKGROUND OF THE INVENTION

The invention relates to a transdermal system for the administration of at least two substances through the skin with the aid of an electric current.

Transdermal systems are generally used to administer a substance, for example a therapeutically active substance or mixture of substances, through the skin of a living organism without the need for clear penetration of the outer layer of the skin—the stratum corneum—and possibly also underlying layers of skin, by mechanical means using a device such as, for example, an injection needle. Transdermal systems are accordingly normally classed as being non-invasive dosage forms.

The great interest in transdermal systems stems from the fact that that dosage form has distinct advantages over other conventional dosage forms. In the case of oral administration undesired side effects frequently occur as a result of incompatibilities in the gastrointestinal tract or the liver. Also, orally administered substances are frequently decomposed or so modified in the gastrointestinal tract or the liver that the desired therapeutic effect does not occur ("first pass" effect). Other forms of parenteral administration, such as, for example, intravenous, subcutaneous or intramuscular injections, involve penetration of the skin or of layers of the skin and are therefore associated by the patient with a sensation of pain. In addition, local inflammation or infection may occur as a result of the partial damage to the skin. Especially in the case of long-term therapy requiring regular injections of the substance or infusions over prolonged periods—often a plurality of times a day—the patient is frequently subjected to a high level of discomfort. This has, among other things, an adverse effect on the co-operation of the patient in adhering to the medically necessary dosage scheme.

Since transdermal systems are not subject to those limitations they are today, especially in the form of one typical example, that is to say the transdermal patch, numbered among the current dosage forms that enjoy widespread usage. Transdermal systems may be divided roughly into passive and active systems. In passive systems the substance to be administered diffuses from a reservoir through the skin. In active systems an additional force promotes the transport of substance through the skin. Especially preferred for that purpose are electric fields, which generate a flow of current through the skin. The administration of a therapeutically active substance through the skin with the aid of an electric current is generally referred to as iontophoresis.

Typically, the iontophoretic systems used today comprise at least two electrodes, one of which forms a contact with the reservoir containing the substance. The other electrode, often referred to as the neutral electrode, is applied directly to the skin and serves to close the circuit via the body. On connection to a source of electrical energy, a current then flows through the skin and transports the substance into the body. In such active systems this is usually accompanied by a passive transport of substance.

A disadvantage of the passive transdermal systems customary today is that the process of diffusion by way of the natural channels of the skin (sebaceous and sweat glands, inter- and trans-cellular transport paths, hair follicles) proceeds very slowly. It is accordingly difficult using a passive transdermal system to administer a substance through the stratum corneum at a dosage rate that is high enough to achieve the desired therapeutic effect. The dosage rate is the amount of substance administered through the skin per unit of time.

Compared with passive transdermal systems, active systems, especially iontophoretic systems, usually enable higher dosage rates to be achieved. An additional advantage of the latter systems is that with them it is possible in a simple manner to influence and alter the dosage rate in a controlled manner. By regulation of the current as the active control element in the administration it is possible, for example, to adapt the dosage rate to the individual requirements of the patient. In addition, therapeutically expedient dosage schemes are feasible, for example it is possible to alternate phases of higher dosage rates with phases of low dosage rates.

In addition, iontophoretic systems have the advantage that the substance to be administered is, as it were, available "on demand". The administration of the substance can be started or stopped by simple activation or deactivation of the electric current flow.

There are, of course, physiologically determined limitations to the current intensities that can be used in iontophoretic systems, since too strong an electric current may result, for example, in burns or other kinds of irritation to the skin. There is therefore a need to control or increase the dosage rate by a means other than merely by way of the intensity of the electric current. One possible method of controlling or altering the dosage rate comprises administering the therapeutically active substance together with a preparation that has an effect on the blood flow in the capillaries of the skin. Such a method is disclosed, for example, in EP-A-0 448 300. In that method, first of all a composition is produced that comprises a vessel-manipulating preparation in addition to the therapeutically active substance. The joint iontophoretic administration is then carried out with that composition. If the vessel-manipulating preparation is one that dilates the vessels, then the blood flow through the capillaries of the skin is increased, resulting in a higher dosage rate of the therapeutically active substance. If the vessel-manipulating preparation is one that contracts the vessels, then the blood flow through the capillaries is reduced, resulting in a depot effect of the therapeutically active substance. Since the vessel-manipulating preparation and the therapeutically active substance are administered together, this process is referred to as "co-iontophoresis".

It is often desirable, for reasons other than for the purpose of controlling the dosage rate, to administer more than one substance iontophoretically using a transdermal system. For example different substances may have different therapeutic effects, or one substance may reduce the undesired side effects of the other substance.

A problem with the transdermal administration of a plurality of substances using currently known iontophoretic systems, however, is that the substances, which are usually contained in the reservoir in the form of different ions, may enter into competition with one another during the iontophoresis; this means that the transport of the charge associated with the current flow is effected by means of a plurality of different charge carriers. This results in it being difficult to control the dosage rates of those substances individually. Reference is expressly made to the problem of competition also in EP-A-0 448 300 which, however, describes only the co-iontophoresis of a therapeutically active substance and a vessel-manipulating preparation. In the case of co-iontophoresis of a vessel-dilating preparation, for example, as the concentration of the vessel-dilating preparation increases, first of all an increase in the dosage rate of the therapeutically active substance is observed, but this is followed by a decrease as the concentration of the vessel-dilating preparation increases further. Consequently, it is necessary first to spend a great deal of time in determining an optimum composition of the therapeutically active substance and the vessel-manipulating preparation in order that the two substances will have the desired effect during co-iontophoresis.

SUMMARY OF THE INVENTION

An aim of the present invention is therefore significantly to increase the efficiency of a transdermal system for the administration of a plurality of substances through the skin with the aid of an electric current, it being possible, in addition, for the administration of the substances to be carried out in a controlled manner. In addition, the transdermal system should be capable of being stored for a prolonged period without there being any appreciable changes in its therapeutic activity as a result.

A transdermal system for the administration of at least two substances through the skin with the aid of an electric current that achieves that aim has the features given in independent claim 1. In accordance with the invention, the transdermal system is accordingly provided with means for the physical separation of the substances by means of which commencement of the administration of the substances one in relation to another is staggered. This controlled sequential administration results in a marked increase in efficiency. Thus, the substance administered first is able fully to develop its effect in the skin before a further substance passes into the skin. For example, a vessel-dilating preparation administered first may increase the blood flow through the capillaries of the skin before a therapeutically active substance is administered, the uptake of that substance thus being improved by the already dilated blood vessels. Time-staggering the administration consequently results in a more efficient utilisation of the individual substances and hence reduces the amount of substance required.

Because in the transdermal system according to the invention the administration of the substances through the skin is staggered in time, in addition the dosage rates for the individual substances can be controlled. Since, for example, at the commencement of the administration essentially only the first substance migrates through the skin, competition effects such as those mentioned hereinabove are virtually absent.

Furthermore, a controlled change in the concentrations of the substances can be effected during use, for example the concentrations of the substances in the transdermal system may be increased, which means that the substances are present in the transfer means in a higher concentration than they were originally in the reservoir. That increase in concentration during use results in a marked increase in the dosage rate, because the substances become concentrated in the vicinity of the skin, with the result that there is an increase in the passive transport rate which accompanies the electrically determined transport of the substances through the skin. It is in addition possible for the substances to be stored in the reservoir in a substantially lower concentration, and for the concentration of the substances to be increased in the transfer means only during use.

In a first preferred example embodiment of the transdermal system according to the invention, the substances are located in a common storage layer contained in the reservoir. The physical separation of the substances occurs when they migrate through a separating layer, which is contained in the transfer means. The separating layer has the property that the various substances have different rates of migration within it. This property results in the physical separation and consequently the sequential administration of the substances.

If, in that example embodiment, the substances are in addition to be increased in concentration, then it is especially advantageous—as explained further below—for the separating layer to be of a higher electrical conductivity than the storage layer.

In a second preferred example embodiment of the transdermal system according to the invention, the reservoir comprises at least two physically separated storage layers each of which contains at least one substance. Especially preferably, there is arranged between the storage layers a modification layer which physically separates the storage layers from one another. A further modification layer may be provided in the transfer means, that layer being so arranged that it is in communication with that storage layer of the reservoir closest to the skin.

In that example embodiment the dosage rates for the substances and the time delay between the administration of the substances can be controlled especially by the thickness of the modification layers between the individual storage layers and by the rates at which the substances migrate through the individual layers.

It is, for example, also possible for the different storage layers to contain the same substance in different concentrations. As a result of the time delay with which the substances contained in the different storage layers are administered, the dosage rate can be variably configured, i.e. modified, as a function of time. This has the advantage that the therapeutic efficiency can be increased even further, because the dosage scheme can be adapted to requirements of a patient as they vary over time.

If, in the second example embodiment, the substances are in addition to be increased in concentration, then it is especially advantageous for the modification layers to be of a higher electrical conductivity than the storage layers.

Further advantageous features and preferred arrangements of the transdermal system according to the invention are disclosed in the dependent claims.

In the following, the invention is explained in detail by way of example embodiments and with reference to the drawings, which are diagrammatic and not to scale.

DETAILED DESCRIPTION OF THE INVENTION

Figure 1:
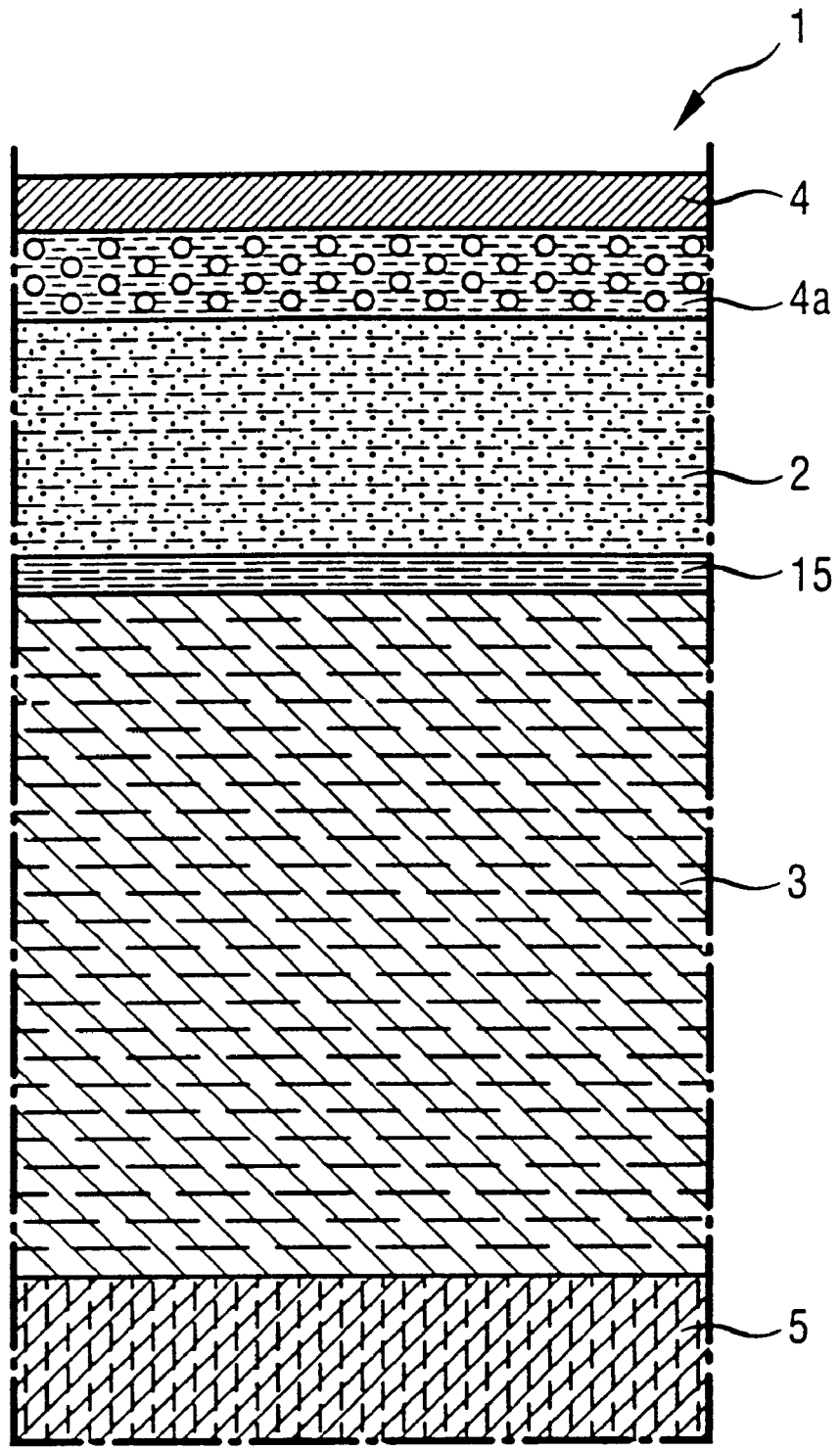
FIG. 1 is a section through part of a first example embodiment of the transdermal system according to the invention showing the fundamental components and FIG. 2 is a section through part of a second example embodiment of the transdermal system according to the invention showing the fundamental components.

For the sake of simplicity, the process according to the invention is described in the following by way of example embodiments in which only two substances are administered transdermally. It is naturally also possible to increase the number of substances administered without going beyond the scope of the invention. FIG. 1 is a diagrammatic representation of a section through part of a first preferred example embodiment of the transdermal system according to the invention for the administration of at least two substances through the skin with the aid of an electric current. For the sake of clarity, only very fundamental components that are important for the understanding of the invention have been shown in FIG. 1. The transdermal system 1 comprises a reservoir, which in this example embodiment consists of a storage layer 2 containing both of the substances, a first substance and a second substance, to be administered. The transdermal system 1 also comprises a separating layer 3 functioning as a transfer means, which layer is connected to both the storage layer 2 and the patient's skin 5 during administration. Also provided in the transdermal system 1 is a first electrode 4, which forms a contact with the storage layer 2. The corresponding counter electrode, often referred to as the neutral electrode, is not illustrated, since only a part of the system has been shown. An intermediate layer 4a between the first electrode 4 and the storage layer 2 is also provided in the transdermal system illustrated in FIG. 1. The system in FIG. 1 also has a blocking membrane 15, which is arranged between the storage layer 2 and the separating layer 3. Details concerning the functions of the intermediate layer 4a and the blocking membrane 15 are given further below.

The storage layer 2 and the separating layer 3 consist of an electrically conductive material so that an electric current can flow through those layers 2 and 3. The storage layer 2 is preferably made of an ionically conductive polymer material, gel or hydrogel in which the substances to be administered are typically contained in dissolved form. The separating layer 3 is also preferably made of an ionically conductive polymer material, gel or hydrogel. The two layers 2 and 3 may be made of the same material. Such polymer or gel materials per se are state of the art and are used frequently in known active and passive transdermal systems.

The first electrode 4, and the counter electrode not shown in FIG. 1, are also state of the art per se, and accordingly do not require any further explanation. The counter electrode may, for example, be so arranged that it surrounds the separating layer 3, as it were in the shape of a ring, and is in direct contact with the skin 5 during administration, similarly to the manner described for the corresponding counter electrode, for example, in WO-A-93/17754. It is, however, also possible to apply the counter electrode to the patient's skin 5 physically separately from the portion of the transdermal system 1 illustrated in FIG. 1, analogously to the arrangement described in the already mentioned EP-A-0 448 300.

To administer the substances, the transdermal system 1 according to the invention is fixed to the patient's skin 5 in such a manner that the side of the separating layer 3 remote from the first electrode 4 is in contact with the skin 2. The transdermal system 1 may be in the form of a patch and may be covered, for example, with an adhesive layer. It is also possible, however, for the separating layer 3 to be in the form of an adhesive layer. The patch is secured to the skin 5 in a manner known per se, as in the case of a conventional transdermal patch. The first electrode 4 and the counter electrode are connected to a source of electrical energy, for example a battery, in such a manner that the energy source, the two electrodes, the storage layer 2, the separating layer 3 and the skin 5 form a closed electric circuit. The substances contained in the storage layer 2 then migrate when their polarity is appropriate, by virtue of an electric field between the electrodes or with the aid of an electric current, from the storage layer 2 through the separating layer 3 into the skin 5.

In the example embodiment shown in FIG. 1, before the iontophoretic administration the first and the second substance are both contained in the storage layer 2 of the reservoir. The two substances may be in a dissolved and electrically charged form, for example in the form of ions. When the electric circuit is closed and the polarity of the ions is appropriate, the ions begin to migrate from the storage layer 2 through the separating layer 3 into the patient's skin 5 by virtue of the prevailing electric field. The rate of migration of ions in a medium is determined essentially by the product of the local electric field strength in the medium and the electrophoretic mobility of the ions. Since, however, the electrophoretic mobility depends on the substance-specific nature of the ions and on the medium in which the ions are moving, the ions of the first substance migrate through the separating layer 3 at a rate of migration that is different from that of the ions of the second substance. Consequently, during migration through the separating layer a physical separation of the ions of the first substance from those of the second substance occurs. If, for example, the ions of the first substance exhibit a higher rate of migration in the separating layer 3 than the ions of the second substance, then the former migrate more rapidly through the separating layer 3 and pass into the patient's skin 5 before the ions of the second substance. As a result of that physical separation of the two substance as they pass through the separating layer, the administration of the two substances can be carried out sequentially, that is to say staggered in time. Since the ions of a substance pass through the separating layer 3 at a substantially constant rate of migration, the time delay between the commencement of the administration of the first substance and the commencement of the administration of the second substance can be controlled by the thickness of the separating layer 3. The thicker the separating layer 3, the greater the time span between the commencement of the administration of the first substance and the commencement of the administration of the second substance. The said time span can, however, also be controlled by the material from which the separating layer is made, since that material influences both the electrophoretic mobility of the ions and the strength of the electric field and accordingly also the difference in the rates of migration of the ions of the two substances.

In accordance with that principle, the transdermal system according to the invention renders possible the controlled sequential administration of two or more substances. This has the great advantage that the substance administered first is able fully to develop its effect in the skin before the second substance passes into the skin. This leads to a more efficient utilisation of the substances and consequently a reduction in the amount of substance required. As a result, either the application time of the transdermal system can be reduced with the dosage rate remaining the same, or the dosage rate can be reduced with the application time remaining the same. Both measures distinctly reduce the irritation to the skin that may occur with conventional iontophoretic systems, because with a shorter application time the electric current flows for a shorter period and with a lower dosage rate an electric current of lower intensity is used.

In addition, the transdermal system according to the invention offers the possibility of altering the concentrations of the two substances in a controlled manner. For example, during the application of the system the concentration of the substances can be increased in the separating layer. This means that the two substances are present in a distinctly higher concentration in the separating layer than they were originally in the storage layer. Preferably, in this variant of the first example embodiment the electrical conductivity of the separating layer 3 is higher than that of the storage layer 2. If the two layers 2 and 3 are made of the same material, the difference in conductivity can be achieved, for example, by means of different degrees of crosslinking of the polymer material. In electrical terms, the separating layer 3 and the storage layer 2 form a series connection of two resistors and, since the electrical conductivity of the separating layer 3 is higher than the electrical conductivity of the storage layer 2, the drop in voltage across the storage layer 2 is greater than the drop in voltage across the separating layer 3. This means, however, that the electric field strength prevailing in the storage layer 2 is higher than that prevailing in the separating layer 3.

For the explanation that follows it is, by way of example, assumed that the electrophoretic mobility of the ions of the first substance in the storage layer 2 is substantially the same as that in the separating layer 3, and that the electrophoretic mobility of the ions of the second substance in the storage layer 2 is substantially the same as that in the separating layer 3. That assumption is purely for the purpose of better understanding, but is not a requirement. Since the rate of migration of the ions of a substance is determined essentially by the product of the local electric field strength and the electrophoretic mobility, it follows, based on the assumption that the mobilities of the ions of a substance in the storage layer 2 and the separating layer 3 are the same, that the rate of migration of that class of ions depends chiefly on the electric field strength in each of the layers 2 and 3. For the above-described variant of the first example embodiment this means that, on passing from the storage layer 2 of lower conductivity and higher electric field strength into the separating layer 3 of higher conductivity and lower electric field strength, the ions of the two substances are "slowed down". The two classes of ions, namely the ions of the first substance and those of the second substance, each considered on its own, therefore have different rates of migration in the two layers 2 and 3. That difference in the rates of migration of a class of ions has the result that the concentration of that class of ions in the separating layer 3, in which the rate of migration is lower, increases. Consequently, during the initialisation of the transdermal system 1 an increase in concentration of that class of ions occurs in the separating layer 3. The same applies also, of course, to the other class of ions. Since, furthermore, in accordance with the invention the two classes of ions move in the separating layer 3 at different rates of migration, in that variant a physical separation of the two classes of ions and, in addition, an increase in the concentration of the two classes of ions, occur in the separating layer 3, which means that the substances become concentrated in the vicinity of the skin 5. This effect has the advantage that the passive transport rate, that is to say the transport rate propelled by the concentration gradient, increases. The passive transport takes place alongside the active transport brought about by the electric field. The net result is a higher dosage rate, achieved without the current intensity having to be increased.

As has already been mentioned above, it is not necessary for the electrophoretic mobility of a class of ions to be the same in the storage layer 2 and the separating layer 3 to achieve the effect of the substances being increased in concentration. The only prerequisite for the increase in concentration is that the rate of migration of a class of ions in the separating layer 3 is distinctly lower than its rate of migration in the storage layer 2. This can also be achieved, for example, if the electric field strength prevailing in the storage layer 2 is the same as that prevailing in the separating layer 3 while the electrophoretic mobility of the class of ions in the two layers 2 and 3 is different. It is naturally also possible to bring about different rates of migration of the class of ions in the two layers 2 and 3 by means of different electric field strengths combined with different electrophoretic mobilities.

The first example embodiment may obviously also be so arranged that, in addition to the physical separation of the substances in the separating layer 3, a reduction in their concentration occurs. This can be achieved, for example, by the separating layer 3 having a lower electrical conductivity than the storage layer 2.

It has so far implicitly been assumed that the two substances present in the storage layer in an electrically charged form have the same polarity. With the transdermal system according to the invention, however, it is also possible for two such substances of which the ions are of different polarity to be administered sequentially. In such a case, the polarity of the electrodes is reversed after administration of the first substance.

In a further development of the first example embodiment there are in addition provided between the first electrode 4 and the storage layer 2 and also, optionally, between the skin 5 and the counter electrode, electrically conductive intermediate layers 4a, which physically separate the first electrode 4 from the storage layer 2, and the counter electrode from the skin. The intermediate layers 4a prevent contamination of the storage layer 2 and of the skin, since any electrolytic products that may be formed at the electrodes during the current flow are kept away from the storage layer 2 and from the skin by means of the intermediate layers 4a.

In another further development of the first example embodiment a blocking membrane 15 is located between the separating layers 3 and the storage layer 2. The blocking membrane 15 has the property that its permeability can be controlled by the application of an electric field. Before application of the transdermal system, the electric field between the electrodes has not yet been switched on and consequently the blocking membrane 15 is virtually impermeable. When the electric field is switched on for the use of the transdermal system, then the blocking membrane 15 is as a result "opened" and the substances to be administered are able to migrate through it. Membranes such as the blocking membrane 15 are state of the art per se.

That further development has the advantage that the transdermal system can be stored better and for longer, since during storage the blocking membrane 15 provides a more durable separation of the storage layer 2 and the separating layer 3, which are, of course, phases that have different physical and chemical properties (for example electrical conductivity). When the transdermal system is inactive, that is to say as long as the circuit has not been closed, the blocking membrane 15 especially prevents any significant transport of mass, for example caused by passive diffusion, between the individual layers. On the other hand, the blocking membrane presents virtually no hindrance to the migration of the substances once the transdermal system for the administration of the substances is in use, that is to say when the membrane is in the opened state.

Figure 2:
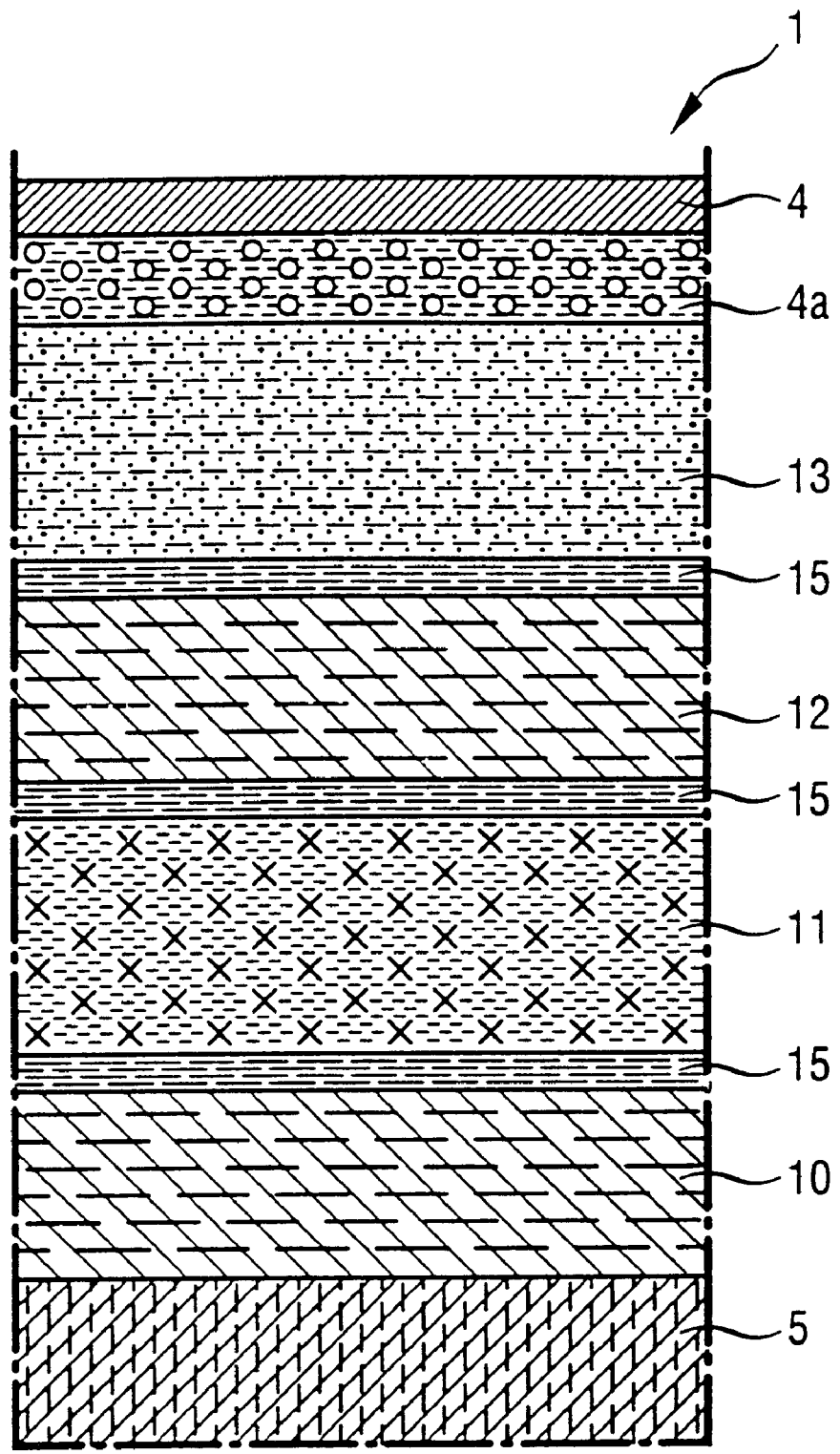

FIG. 2 is a diagrammatic representation of a section through part of a second preferred example embodiment of the transdermal system according to the invention. For the sake of clarity, only very fundamental components that are important for the understanding of the invention have been shown in FIG. 2. The transdermal system 1 comprises a reservoir, which in this example embodiment contains a first storage layer 11, and a second storage layer 13 physically separated from the first. Contained in the first storage layer 11 is a first substance to be administered and contained in the second storage layer 13 is a second substance to be administered. Provided between the two storage layers 11 and 13 is a first modification layer 12, which physically separates the two storage layers 11 and 13 from one another. The transfer means consists of a second modification layer 10, which on application of the transdermal system is connected to both the patient's skin 5 and the first storage layer 11. The four layers 10–13 mentioned form a stack-like arrangement. Also provided in the transdermal system 1 is a first electrode 4, which forms a contact with that side of the second storage layer 13 remote from the skin 5. The corresponding counter electrode is not illustrated, since only a part of the system has been shown. An intermediate layer 4a between the first electrode 4 and the second storage layer 13 is also provided in the transdermal system shown in FIG. 2. The system in FIG. 2 also has blocking membranes 15, which are arranged between the first modification layer 12 and the adjacent storage layers 11 and 13, and between the second modification layer 10 and the first storage layer 11. Details concerning the functions of the intermediate layer 4a and the blocking membranes 15 are given further below.

The two storage layers 11 and 13 and the two modification layers 10 and 12 consist of an electrically conductive material, so that an electric current can flow through those layers 10–13. The storage layers 11 and 13 are preferably made of an ionically conductive polymer material, gel or hydrogel in which the substances to be administered are typically contained in dissolved form. The modification layers 10 and 12 are also preferably made of an ionically conductive polymer material, gel or hydrogel. All four layers 10–13 may be made of the same material. Such polymer or gel materials per se are state of the art and are used frequently in known active and passive transdermal systems.

With respect to the electrodes, the same explanations as those given hereinbefore in connection with the first example embodiment apply analogously.

To administer the substances, the transdermal system 1 according to the invention is fixed to the patient's skin 5 in such a manner that that side of the second modification layer 10 remote from the first electrode 4 is in contact with the skin 5. The transdermal system 1 may be in the form of a patch and may, for example, be covered with an adhesive layer, or the second modification layer 10 may be in the form of an adhesive layer. The system is then secured to the skin 5 in a manner known per se as in the case of a conventional transdermal patch. The first electrode 4 and the counter electrode are connected to a source of electrical energy, for example a battery, in such a manner that the energy source, the two electrodes, the storage layers 11 and 13, the modification layers 10 and 12 and the skin 5 form a closed electric circuit. The first substance contained in the first storage layer 11 then migrates when the polarity of the substance is appropriate, by virtue of an electric field between the electrodes or with the aid of an electric current, from the second storage layer 11 through the second modification layer 13 into the skin 5. In an analogous manner, the second substance migrates from the second storage layer 13 through the first modification layer 12, through the first storage layer 11 and through the second modification layer 10 into the skin 5.

In this second example embodiment of the transdermal system according to the invention, the two substances are contained in different storage layers 11 and 13 of the system that are physically separated from one another. During the iontophoretic administration the electric current flows from the first electrode 4 through the second storage layer 13, the first modification layer 12, the first storage layer 11, the second modification layer 10 and the patient's skin 5 to the counter electrode, thereby causing the substances to be transported into the skin 5. Since the ions of the first substance, which is contained in the first storage layer 11, have to migrate through only the second modification layer 10 in order to pass into the skin 5, they reach the skin 5 significantly earlier than the ions of the second substance contained in the second storage layer 13, which have to migrate in addition through the first modification layer 12 and the first storage layer 11 before they reach the skin 5. The transdermal system thus renders possible the sequential administration of the two substances.

The delay between administration of the first and the second substance can be influenced in a controlled manner also in that example embodiment. The delay can be controlled, for example, by the thickness of the first modification layer 12. Thus, a greater thickness of the first modification layer 12 results in a longer period of delay. It is, however, also possible to control the delay between administration of the first and second substances by means of the rate of migration of the associated ions. As has already been mentioned hereinbefore, the rate of migration of a class of ions in a medium depends both on the local electric field strength in the medium and on the electrophoretic mobility of the class of ions in that medium. Thus, the delay which, of course, is dependent essentially on the time required by the ions of the second substance to migrate through the first modification layer 12, can be influenced in a controlled manner by the electric field strength in the first modification layer 12 and by the electrophoretic mobility of the ions of the second substance in that first modification layer 12. The electric field strength in the first modification layer 12 can in turn, as explained hereinbefore, be controlled by the electrical conductivity of that layer 12. Thus, for example, when the electrical conductivity of the first modification layer 12 is high in comparison with that of the second storage layer, the rate of migration in that modification layer 12 will be distinctly lower. In that manner the second example embodiment of the transdermal system according to the invention renders possible controlled sequential administration of the two substances.

It is also possible in that example embodiment to increase the concentration of the substances in the second modification layer 10, i.e. in the immediate vicinity of the skin 5, in order thereby to increase the passive transport rate and consequently the total dosage rate. For that purpose, for example, the transdermal system may be so constructed that the conductivity of the two modification layers 10 and 12 is distinctly higher than that of the storage layers 11 and 13, resulting in a lower electric field strength and consequently in a lower rate of migration of the ions in the modification layers 10 and 12. The electrical conductivity of the individual layers 10–13 can be controlled, for example, by means of the degree of crosslinking of the polymer material. During the iontophoretic administration the first substance migrates from the first storage layer 11 into the second modification layer 10, where its concentration is increased, and it then passes into the skin 5. The second substance migrates first from the second storage layer 13 through the first modification layer 12 in which it has a low rate of migration, that is to say in which it has, as it were, "waits", then migrates at a higher rate of migration through the first storage layer 11, and is subsequently increased in concentration in the second modification layer 10.

It is, however, also possible for the two substances contained in the physically separated storage layers 11 and 13 to be chemically identical and, for example, to differ in that they are present in the two storage layers 11 and 13 in different concentrations. This has the advantage that, with the field strength being kept constant, the dosage rate can be arranged to be variable as a function of time and can thus be adapted to the therapeutic requirements of a patient as they vary over time. For that purpose, for example, the first storage layer 11 may contain the substance in a lower concentration than the second storage layer 13. The substance from the first storage layer is then administered first and, staggered in time in the manner described hereinbefore, the same substance is administered from the second storage layer. Since the substance is present in a higher concentration in the second storage layer, after it has migrated through the first modification layer 12 and the first storage layer 11 it is present in the second modification layer 10 in a higher concentration than that of the substance originating from the first storage layer 11 previously. This results at least in an increase in the passive transport rate and consequently an increase in the total dosage rate.

In a further development of the second example embodiment, there are in addition provided between the first electrode 4 and the second storage layer 13 and also, optionally, between the skin 5 and the counter electrode, electrically conductive intermediate layers 4a, which physically separate the first electrode 4 from the second storage layer 13, and the counter electrode from the skin. The intermediate layers 4a prevent contamination of the second storage layer 13 and of the skin, since any electrolytic products that may be formed at the electrodes during the current flow are kept away from the second storage layer 13 and from the skin by means of the intermediate layers 4a.

In another further development of the second example embodiment blocking membranes 15, as described hereinbefore, are located between the modification layers 10 and 12 and the storage layers 11 and/or 13 adjacent thereto. The shelf life of the transdermal system can thereby be improved.

It is naturally also possible for the reservoir of the transdermal system to contain more than two storage layers for more than two substances to be administered. It is especially advantageous for further modification layers to be arranged between adjacent storage layers and for the individual layers optionally to be physically separated by further blocking membranes. This is effected in a manner analogous to that explained above for the second example embodiment.

Using the transdermal system according to the invention it is thus possible to administer at least two substances sequentially, that is to say staggered in time, in a controlled manner by iontophoretic means. This results in a marked increase in efficiency, since the first substance is able fully to develop its effect in the skin before the second substance is administered. For example, the first substance may be a vessel-dilating preparation. In that case the second substance reaches the vessels only after they have been dilated by the first substance, with the result that the second substance has a more rapid and more efficient action. In another example, the first substance may cause contraction of the blood vessels, as a result of which a depot effect can be achieved for the substance administered subsequently. In another example, the first substance is a pain- or inflammation-inhibiting preparation that reduces side effects and accompanying symptoms of the transdermal administration.

What is claimed is:

1. A transdermal system (1) for the administration of at least two substances through the skin with the aid of an electric current, the transdermal system (1) comprising:
   (a) a reservoir having a storage layer (2) and containing at least two substances,
   (b) transfer means connected to said reservoir and adapted to be connected to the skin (5) during administration, the transfer means comprising a separating layer (3) adapted to physically separate the substances from one another as they pass through the separating layer (3); and
   (c) electrodes (4) adapted to generate a current to transport the substances from the reservoir through the transfer means into the skin (5).

2. A transdermal system of claim 1, wherein the different substances are present in the storage layer (2) in an electrically charged form, the polarity of the electric charge being the same for the different substances.

3. A transdermal system of claim 1, wherein the different substances are contained in the storage layer (2) in an electrically charged form, the polarity of the electric charge being different for the different substances.

4. A transdermal system of claim 1, wherein the electrical conductivity of the separating layer (3) is different from that of the storage layer (2).

5. A transdermal system of claim 4 wherein the electrical conductivity of the separating layer (3) is higher than that of the storage layer (2).

6. A transdermal system of claim 1, wherein the separating layer (3) comprises a polymer material, a gel, or a hydrogel.

7. A transdermal system of claim 1, wherein the storage layer (2) comprises a polymer material, a gel, or a hydrogel.

8. A transdermal system of claim 1, wherein there is provided at least at one electrode (4) an intermediate layer (4a) which is adjacent to said electrode (4) and which is adapted to keep electrolytic products away from the storage layer (2) and from the skin.

9. A transdermal system of claim 1, wherein there is provided between the storage layer (2) and the separating layer (3) a blocking membrane (15) the permeability of which can be altered by means of an electric field.

10. A transdermal system of claim 1, wherein the reservoir comprises at least a first storage layer (11) and a second storage layer (13) that are substantially separated from one another physically, each layer containing at least one substance.

11. A transdermal system of claim 10, wherein there is provided between the storage layers (11, 13) a modification layer (12) which physically separates the storage layers (11, 13) from one another.

12. A transdermal system of claim 11, wherein the transfer means comprises a second modification layer (10) which is in physical communication with that storage layer (11) of the reservoir adapted to be closest to the skin (5).

13. A transdermal system of claim 12, wherein the electrical conductivity of the modification layers (10, 12) is different from that of the storage layers (11, 13).

14. A transdermal system of claim 13 wherein the electrical conductivity of the modification layers (10, 12) is higher than that of the storage layers (11, 13).

15. A transdermal system of claim 10, wherein the storage layers (11, 13) comprise a polymer material, a gel, or a hydrogel.

16. A transdermal system of claim 12, wherein the modification layers (10, 12) comprise a polymer material, a gel, or a hydrogel.

17. A transdermal system of claim 10, wherein there is provided at least at one electrode (4) an intermediate layer (4a) which is adjacent to said electrode and which is adapted to keep electrolytic products away from at least one of the storage layers (11, 13) and from the skin.

18. A transdermal system of claim 12, wherein there are provided between adjacent modification layers (10, 12) and storage layers (11, 13) blocking membranes (15) the permeability of which can be altered by means of an electric field.

* * * * *